United States Patent [19]

Henderson

[11] Patent Number: 5,073,402
[45] Date of Patent: Dec. 17, 1991

[54] METHOD OF MAKING AN OPTICAL DEVICE

[75] Inventor: Brian Henderson, Ayrshire, United Kingdom

[73] Assignee: Medical Laser Technologies Limited of Research Park, Edinburgh, Scotland

[21] Appl. No.: 493,970

[22] Filed: Mar. 15, 1990

[30] Foreign Application Priority Data

| Mar. 16, 1989 | [GB] | United Kingdom | 8906073 |
| Sep. 7, 1989 | [GB] | United Kingdom | 8920230 |
| Feb. 13, 1990 | [GB] | United Kingdom | 9003165 |

[51] Int. Cl.$^5$ .................. A01N 1/02; B05D 3/06; B05D 5/06
[52] U.S. Cl. .................. 427/2; 427/53.1; 427/54.1; 427/163; 427/169
[58] Field of Search .......... 427/2, 53.1, 54.1, 55, 427/163, 164, 165, 169

[56] References Cited

U.S. PATENT DOCUMENTS

| 4,067,937 | 1/1978 | Unno et al. | 427/163 |
| 4,322,164 | 3/1982 | Shaw et al. | 356/41 |
| 4,338,352 | 7/1982 | Bear et al. | 427/53.1 |
| 4,425,375 | 1/1984 | Abramson | 427/163 |
| 4,660,925 | 4/1987 | McCaughan, Jr. | 350/96.15 |
| 4,792,675 | 12/1988 | Laughlin | 250/227.28 |
| 4,878,492 | 11/1989 | Sinofsky et al. | 128/395 |
| 4,878,725 | 11/1989 | Hessel et al. | 350/96.15 |
| 5,006,314 | 4/1991 | Gourley et al. | 427/2 |

Primary Examiner—Shrive Beck
Assistant Examiner—Marianne L. Padgett
Attorney, Agent, or Firm—Ratner & Prestia

[57] ABSTRACT

A method of making an optical device is described, in which an optical fibre having a free end is provided. The free end of the optical fibre is contacted with a curable material and the material on curing is capable of forming around the free end, a member having light-scattering properties. The material is cured in a manner to produce the member with an isotropic surface. Typically, the curable material contacted by the free end is in the form of a droplet suspended in a liquid and the material is preferably cured by passing laser radiation along the optical fibre towards its free end.

9 Claims, 5 Drawing Sheets

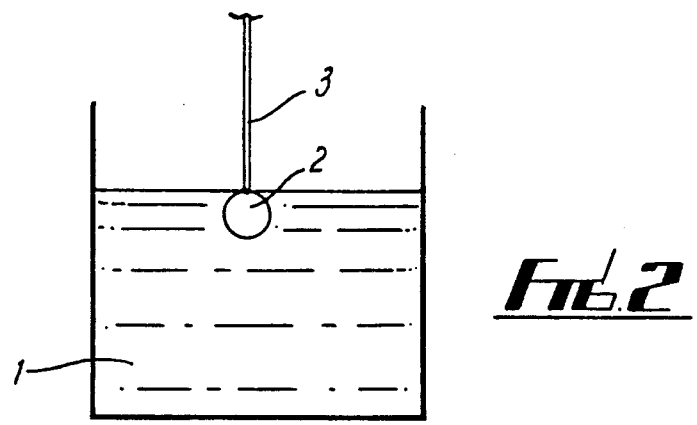
_FIG.2_
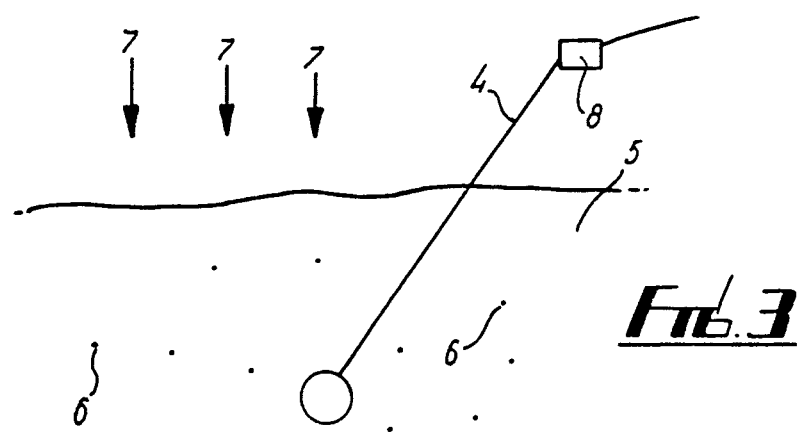
_FIG.3_
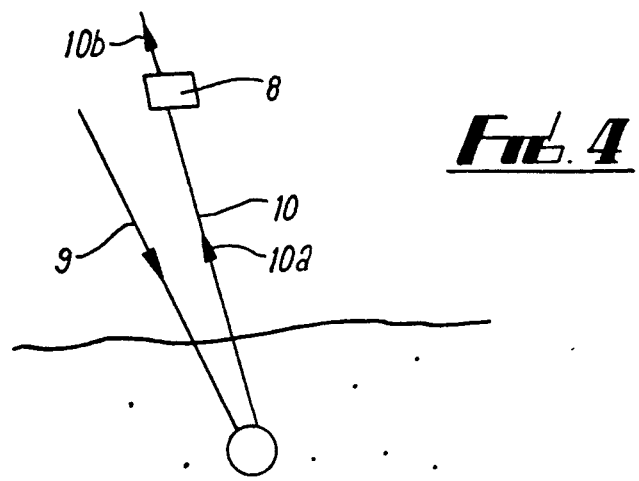
_FIG.4_

METHOD OF MAKING AN OPTICAL DEVICE

This invention relates to a method of forming an emitter or detector surface on the end of an optical fibre.

BACKGROUND OF THE INVENTION

There are various applications where it is desirable to pass light down an optical fibre and to emit the light substantially isotropically (that is, with equal energy density in all directions) from the remote end of the fibre, or to receive substantially isotropically at the remote end and transmit it along the fibre. One such application is in medical endoscopy, where it is desirable to be able to measure the intensity of light energy actually reaching a treatment site. This could best be done by a detector which is isotropic, which is sufficiently small and flexible to pass through an endoscope, and which is formed of clinically compatible materials.

It has been attempted to form an isotropic emitter/detector by bonding a sphere of a light-scattering material such as PTFE to the end face of an optical fibre. It is difficult to form a satisfactory bond, and there is a substantial risk of the bond failing in use. It is also difficult to machine the spherical member accurately, a typical diameter being about 1 mm.

SUMMARY OF THE INVENTION

According to the present invention there is provided a method of making an optical device, comprising:
providing an optical fibre having a free end;
contacting said free end with a curable material which on curing is capable of forming around said free end a member having light-scattering properties; and
curing said material in a manner to produce said member.

The present invention overcomes or mitigates the problems of the prior art methods, and provides an optical device which can be used as an isotropic emitter or detector and which can be made relatively easily and with a high degree of repeatability.

Typically, the member is formed to enable it to emit or detect light substantially isotropically. However, for some applications the member could be formed to emit or detect light in a predetermined non-isotropic pattern. This could be done by moulding the member to a desired shape or moulding a shaped cover around the member after the member has been produced.

Preferably, the curable material contacted by the free end is in the form of a droplet suspended in a liquid. The material is preferably cured by passing laser radiation along the optical fibre towards its free end. Typically, the radiation may be ultra-violet light, visible light or near infra-red light.

Preferably the curable material comprises a chemical resin and a catalyst that induces curing of the resin by absorbing radiation with a wavelength in the ultra-violet, visible or near infra-red regions of the spectrum. Typically, the resin could be a methacrylate and is preferably methyl methacrylate. Typically, the curable material has a viscosity which enables it to be suspended in an organic liquid such as paraffin to produce a spherical probe end.

Preferably the material has sealant properties; a particularly effective material is a dental fissure sealant such as that sold by Voco Chemie under the Trade Mark FISSURIT. FISSURIT is provided in uncured liquid form and is cured by application of blue-green laser light to form solid mass around the free end of the fibre. In this case the catalyst has an absorption band centred at about 467 nm.

Typically, the material also comprises a filler material which scatters, in use, light emitted by the fibre or collects light to enable the light to be transmitted by the fibre. Preferably, the filler material scatters or collects the light isotropically and could be a material such as $TiO_2$ or $SiO_2$.

The fibre is preferably resistant to high temperature and capable of being produced with a small overall diameter. A suitable fibre is that sold by Polymicro Technologies under the designation FLP 100110125, which can be provided with an overall diameter of 125 $\mu$m.

The optical device may include two or more optical fibres, each of which has a free end which is contacted with the curable material.

According to the second aspect of the present invention there is provided a method of treating tissue, comprising inserting a light-emitting device into animal tissue and passing light along said device to irradiate the tissue. The light-emitting device is preferably substantially isotropic.

According to a third aspect of the present invention there is provided a method of determining the activity of a drug during its use in treatment of animal tissue by examining the fluorescence of the drug, comprising inserting an optical device into the tissue, irradiating said tissue to cause the drug to fluoresce, and detecting the fluorescence produced.

Radiation from the range of visible (green) light to near infra-red light may be used.

Preferably, an infra-red wavelength for example 1.06 $\mu$m is used for treating tissue, as infra-red light provides effective and gradual penetration and does not burn the tissue.

However, if it is the fluorescent characteristics of a drug that are to be monitored, a different wavelength may be more useful. For example, to induce fluorescence of 632 nm could be used.

The optical device of the third aspect of the present invention may be used either to induce or to detect fluorescence. It may also be adapted to perform both functions; for example, by either including two fibres in one device, or using a single fibre with appropriate optical equipment to differentiate between incoming and outgoing light. If two fibres in one device are used, one fibre may be used to provide light and the other to detect light. The optical properties and constants of tissue may be examined by the use of such a device, for example, light can be provided at one wavelength along one of the two fibres and the reflected light can be examined at the same wavelength along the other.

If used in photodynamic therapy, the device can be used to monitor the efficacy of a drug by examining its fluorescent characteristics. The detected light travels from the probe end through a filter which removes light of the wavelength used to induce fluorescence, for example 632 nm, allowing the fluorescence alone, for example 692 nm, to be detected.

Preferably, the material used in making the probe end is selected for its low absorption of light in these ranges.

According to a fourth aspect of the present invention there is provided a method of tissue optical parameter measurement employing an optical device comprising an optical fibre, one end of which comprises a isotropic light emitter/detector, the method comprising embedding the fibre and emitter/detector in the tissue supplying light, through the fibre to the emitter/detector and detecting the quantity of light reflected from the tissue.

Preferably, laser light is used. Most preferably of a visible wavelength such as approximately 630 nm from a HeNe laser.

Preferably, the isotropic emitter includes impurities of a material such as $TiO_2$ or $SiO_2$ which scatter the light in all directions equally.

The optical device may be calibrated by submerging the emitter/detector in a fluid, and determining the background signal by detecting the quantity of light reflected by the fluid. Preferably, the fluid is water.

The corrected reflectance readings are given by taking reflectance readings in the method described above and subtracting the calibration reading for reflectance of clean water also determined as described above.

The device may be used for a number of purposes including measurement of the oxygenation of blood and symmetry of tissue.

The device may also be used to determine the depth profile of tissue, that is the light intensity measurement obtained versus depth of tissue which may be used to determine the effect of treatment on the tissue and the dosage of light used in cancer treatment may be adjusted as necessary.

Preferably, the depth profile is determined by irradiating the tissue from above and embedding the fibre and detector in the tissue at various depths and detecting the light intensity.

The dosage may be increased by increasing illumination from above or by using a fibre and emitter embedded in the tissue for in situ illumination.

Preferably, one fibre is used to supply light to the emitter/detector and to return light for measurement.

The fibre may be coupled to a second fibre, out with the tissue, which leads to a measurement detector.

Alternatively, a supply and a separate detector fibre may be embedded in the emitter/detector.

According to a fifth aspect of the present invention there is provided a method of introducing the optical fibre and emitter/detector into the tissue comprising inserting a hypodermic syringe needle into the tissue passing the fibre and emitter detector through the needle and into the tissue, and removing the needle.

Preferably, the fibre is of the order of 50 um in diameter.

According to a sixth aspect of the present invention there is provided an optical fibre, for use in the optical device, the fibre comprising a plurality of spaced sequential markings along its length.

Typically, the markings are equally spaced.

Preferably, the markings on the fibre are formed from spots of substantially the same light cured resin as used in the emitter/detector.

Preferably, the markings are spaced at 1 cm intervals. Most preferably, every 5th and/or 10th mark is coloured so as to make counting the markings easier.

According to a seventh aspect of the present invention there is provided a less delicate and less easily damaged optical fibre comprising an optical fibre clad in a moulded material.

Preferably, the cladding enables the transmission of light and does not include scattering impurities.

According to an eighth aspect of the present invention there is provided a fibre mount comprising a standard syringe, the fibre being passed through the syringe end positioned centrally in the syringe by a tapered plug with a small diameter central bore which receives the fibre, when the plug is in position in the syringe.

Preferably, the plug is formed from a plastics material.

Preferably, the syringe is threaded for attachment to an optical detector or standard mount. According to a ninth aspect of the present invention there is provided a fibre probe for use in detecting arterial plaque, the probe comprising an optical fibre one end of which includes an isotropic emitter, a length of the fibre adjacent the isotropic emitter being clad in a light cured moulded material optically transparent in the wavelength range covering the fluorescence from artery plaque and the input wavelength to form a cylindrical detector.

The length of the cylindrical detector enables the detection of light over a longer length of the artery than would have been possible with the isotropic detector.

Preferably, the material from which the detector is formed includes scattering impurities such as $TiO_2$ and $SiO_2$.

Preferably, a plurality of fibres are embedded in the cylindrical detector, the fibres transmitting the detected light back to a monitor and thus providing a directional indication of plaque positioned on the artery walls.

Preferably, the cylindrical detector is formed by placing a plastic sheath over the fibre, inserting light curable moulding material into the space between the sheath and the fibre, passing light down the fibre in order to cure the material, and peeling off the sheath.

Most preferably, the sheath is formed from a material with a low coefficient of friction such as P.T.F.E.

As the plaque is fluorescent the isotropic emitter may be used simply to excite fluorescence in the plaque, which may be detected by the cylindrical detector.

BRIEF DESCRIPTION OF THE DRAWINGS

Embodiments of the present invention will now be described by way of illustration in the following Examples and with reference to the accompanying drawings in which:

FIG. 2 illustrates, schematically, a second method of making an optical device;

FIG. 3 illustrates a first method of detecting the fluorescence of a drug;

FIG. 4 illustrates a second method of detecting the fluorescence of a drug;

DESCRIPTION OF PREFERRED EMBODIMENTS

Figure 1A:
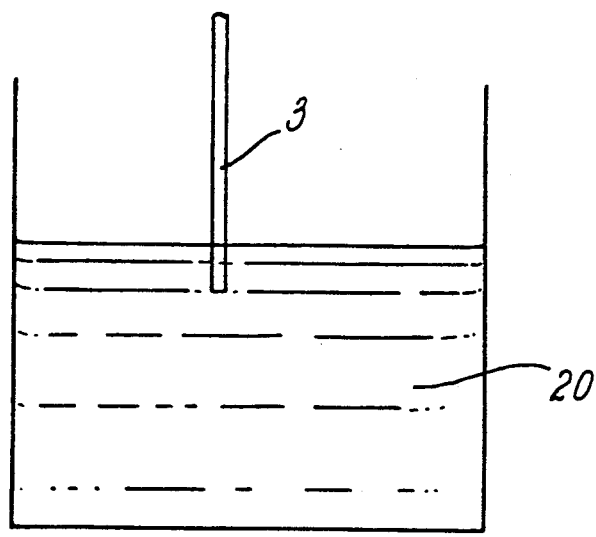
FIGS. 1A and 1B illustrate, schematically, a first method of making an optical device.

Photocurable materials are generally based upon a methacrylate combined with a photoinitiation system which provides free radicals in the presence of blue light. The rate of photoinitiation equals the rate of production of free radicals and is given by the product of the quantum yield of the photoinitiation times the amount of radiation absorbed by the photosynthesizer. Hence the depth of cure of these materials, or the volume of cure, is related to the absorption coefficient of the photosynthesizer and the amount of light available for curing.

The success of the cure relies on the absorption of photons from the irradiation beam by the photoinitiator. The depth of cure is therefore limited if the incident photon flux is insufficient to provide the desired cure within a certain time. Larger cure depths will consequently be obtained by a material with a low absorption coefficient at the curing wavelength. All organic systems absorb at ultra-violet wavelengths (<350 nm), but only the peak of the photoinitiation absorption at 450 nm or greater contributes significantly within this material and larger cure depths may be possible.

Equally, moving away from this peak towards higher wavelengths ensures a trade-off between absorption and cure time for the desired cure depth. It should be noted that obviously at the absorption bands of the photoinitiation system light transmission will be reduced. Hence, the blue light curing compound within the material gives the uncured polymer a yellow hint. It has been suggested, however, that this may be reduced through photobleaching the initiator by delivering an intense curing flux. In order to achieve the requirement of a diffusing material suitable for probe usage, a light-scattering filler must be added to the light cured polymer. The contribution to light distribution within the polymer and its cure will be affected by the degree of scatter introduced by the filler. Generally, the depth of cure will be reduced due to the diffuse nature of the flux giving the photon the increased opportunity to be absorbed at a smaller depth. However, with attention given to this effect, the diffuse light distribution, and its resulting curing action, may be manipulated to obtain a variety of configurations for optical devices.

Much of the recent development work on light cured polymers at blue photoinitiation wavelengths has evolved from applications in dentistry. These resin-based restorative materials were primarily used as dental fissure sealants. Consequently, the light cured polymer contained a filler to enable the cured material to have a white enamel appearance similar to that of teeth. These aesthetic additives were most often powdered titanium dioxide, silicon dioxide, radro-opaque glass, barium sulphate, etc. and were used not only to give the desired appearance, but also mechanical strength to the polymer. Clearly, the extent of the light-scattering within the polymer can be controlled by the quantity of filler added. Hence, the choice of such a material for probe use would appear very promising due to the ability to tailor the optical properties, i.e. scattering, to suit the required light distribution.

The main companies producing opaque or white dental fissure sealants is shown in Table 1. All the brands of materials detailed are blue light cured, (400-470 nm) and the physical and chemical properties are well reported.

TABLE 1

| Brand | Manufacturer |
| --- | --- |
| Delton LC Opaque | Johnson and Johnson, East Windsor, USA |
| Roltseal LC | Kulzer, Wehrheim, |

TABLE 1-continued

| Brand | Manufacturer |
| --- | --- |
| Melroseal | West Germany Vivadent, Schaan Liechtenstein |
| Primashield | Chaulk/Dentsply, Milford, USA |
| Resto-seal A | Den-Mat, Scinta Manta, USA |
| Verite-sheen | Unitek, Monrovia, USA |
| Folofil | ICI Ltd, Macclesfield, Cheshire, UK |
| Lee-fill | Lee Pharmaceuticals, South El Monte, CA, USA |
| Fissurit, Opaque | Voco, Chemie, Cuxhaven, West Germany |

Typically, all dental fissure sealants must have the following desiderata:
Cure in blue light (400-470 nm);
Cure quickly;
Cure to a complete rigid form;
Bond to many surfaces, e.g. ceramic, enamel, etc;
No interaction between cured state and its environment;
Non-toxic (BS 5825:1989);
Minimal water absorption;
Minimal shrinkage of cure.

Of course, all of these requirements are relevant to a light dosimetry probe. However, of particular interest in probe fabrication is the fact that these materials will have had some form of toxicity testing and have a strong mechanical form when cured. The use of a material with an established medical application greatly enhances its choice over non-medical alternatives. Also of interest is the temperature stability of these polymers. This is typically quoted as 150° C., which is significantly higher than any temperature that would be expected in photodynamic therapy of tissue. Therefore, both physically and chemically, these materials are ideal for probe application by conforming to the requirements for optimum probe design.

EXAMPLE 1

FLP 100110125 optical fibre from Polymicro Technologies, having an outside diameter of 125 um, is cleaned at both ends, with its buffer coat intact to the cleaned ends. An argon ion laser, which produces blue-green light, is then focused into the fibre through a lens and the exiting beam is examined to ensure that it has a clean profile.

Figure 1B:
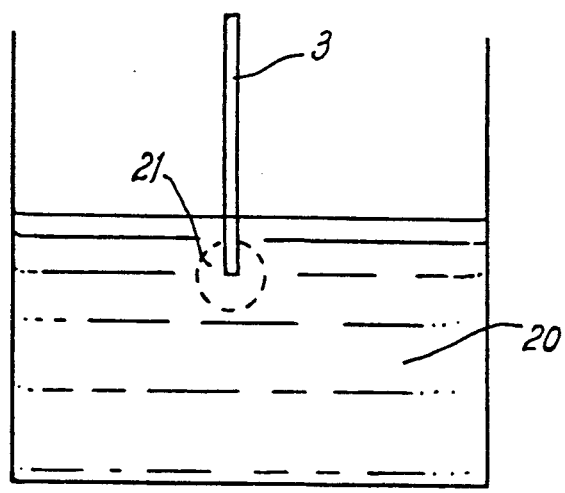

With the laser switched off, the exit end of the fibre 3 (FIG. 1A) is immersed in uncured liquid FISSURIT (Trade Mark) 20 solution from Voco Chemie, and the laser is then actuated to pass its blue-green light along the fibre. The light emerging from the immersed end effects polymerisation of the FISSURIT material to produce a solid mass 21 (see FIG. 1B) around the fibre end. By adjusting the amount of light produced by the laser and the length of time of laser actuation the shape and size of the solid mass can be controlled, and an isotropic surface can be easily produced.

The isotropy is checked on removal of the fibre end from the liquid 20 and after removing excess liquid from the cured mass 21. When the required size and shape of the mass 21 have been produced the light from the laser is increased and sustained to ensure complete curing.

Further products can be produced in a matter of seconds once the power of the laser and the length of time of its actuation have been established, as checking of the isotropy will not then be necessary.

EXAMPLE 2

A FLP100110125 optical fibre from Polymicro Technologies, having an outside diameter of 125 um is prepared as described in Example 1.

A drop of light-curable material such as the dental fissure sealant FISSURIT (Trade Mark) sold by Voco Chemie, is added to paraffin 1 (see FIG. 2). Due to surface tension the droplet 2 suspends from the surface of the paraffin 1, as shown in the drawing. An optical fibre 3 is brought into contact with the droplet 2 so as just to penetrate the droplet 2, and laser light of 488 nm is passed along the fibre 3 to cure the droplet 2. The whole device is then removed from the paraffin 1.

The above method results in a transparent spherically-shaped probe end which acts as a lens, i.e. it can change the divergence of light falling on tissue. Different shaped probe ends may be obtained by varying the depth to which the fibre 3 penetrates the droplet 2. Other shapes may be obtained by the use of moulds.

The nature of the FISSURIT material ensures that a hard seal is produced on curing, and the cured material adheres firmly to the fibre. The cured material is non-toxic and medically compatible, and excellent isotropy can be produced.

Both the isotropic and the lens devices can be used in a variety of applications, medical and non-medical, where internal emission and/or detection of light is necessary.

In medical use, visible light is absorbed strongly by tissue, and so tends to burn rather than penetrate the tissue. Infra-red light is chosen in medical treatment of tumours and malignant tissue for its greater penetration.

Because of the low resistance of living cells to excessive heat, the device may be used to eradicate tumours. It may do this with a precision lacking in present technology due to the shape of the probe end and the ease with which the device can be placed internally in the body at the desired location, and so can be operated with the minimum of damage to healthy tissue.

The device may also be used for clearing arteries in angioplasty. The device, with its shaped probe end, may be fed into the artery and a laser may be used to fire light in predetermined patterns at the artery wall. A balloon device may then be used to push back the warmed artery wall.

These patterns are determined by the wavelength used and by the shape of the probe end, which may be in the form of a lens for distributing light as desired. Because different wavelengths react differently with the same shaped device, the pattern of light hitting the artery wall could be varied to suit the local circumstances as they change along the artery by suitable choice of wavelength used.

Fluorescence of Drugs

The activity of many drugs used in medical treatments can be monitored by examining changes in the drug's fluorescence at specific wavelengths (see FIG. 3). Tissue 5 is treated with a drug, which is absorbed as indicated at 6, and the tissue 5 is irradiated, as indicated at 7, at 488 nm to cause fluorescence of the drug. The level of fluorescence is then detected via an isotropic probe 4 which passes the detected light through a filler 8 for removing the light of irradiation and thence to a detector (not shown).

The probe 4 may also be used to irradiate the tissue 5 (see FIG. 4), or a separate probe may be used for each function. If it is the same probe, then it is preferable to use two optical fibres 3a, 3b, (FIG. 4) terminating within the same sphere for emission 9 and detection 10 of the light respectively. Arrow 9 represents incoming light of irradiation and arrow 10b is light to be monitored after the light of irradiation and fluorescence 10a have been separated at 8. It is also possible to use a single fibre for both these functions.

This process can also be applied to detect the presence of viruses to which drugs are attached, and to obtain information about their content.

A further advantage of the device is that some embodiments of an isotropic probe end in accordance with the second aspect of the present invention may also be considered as an integrating sphere: all light inside the probe is evenly distributed and is the same at all internal points. Existing integrating spheres are large, and the present invention allows this effect to be created inside the body.

Figure 5:
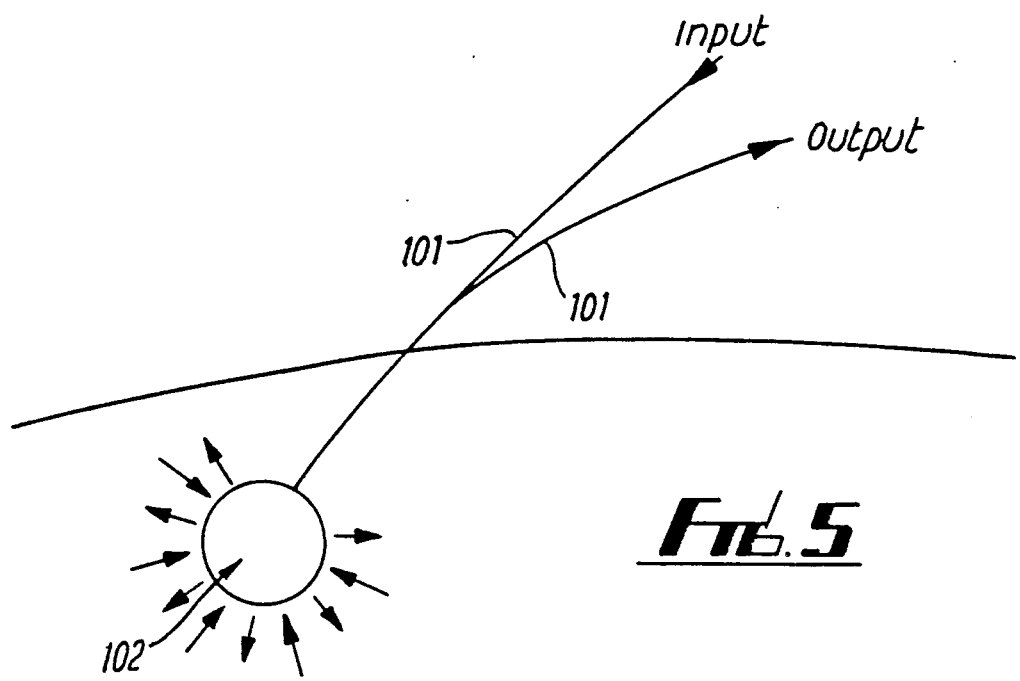
FIG. 5 shows a schematic diagram of an optical device being used in tissue diagnosis.

FIG. 5 shows a method of tissue optical parameter measurement wherein an optical fibre 101, one end of which comprises an isotropic light emitter/detector 102 is embedded in the tissue and light is supplied through the fibre 101 to the emitter/detector 102 which emits light into the tissue and detects light reflected from the tissue. A HeNe laser is used to supply the light required at a wavelength of approximately 630 nm.

One fibre may be used to supply light to the emitter/detector and to return light for measurement or a second fibre 1 may be coupled to the first to return light for measurement or the second fibre 1 may be embedded in the emitter/detector for the same purpose.

Figure 6:
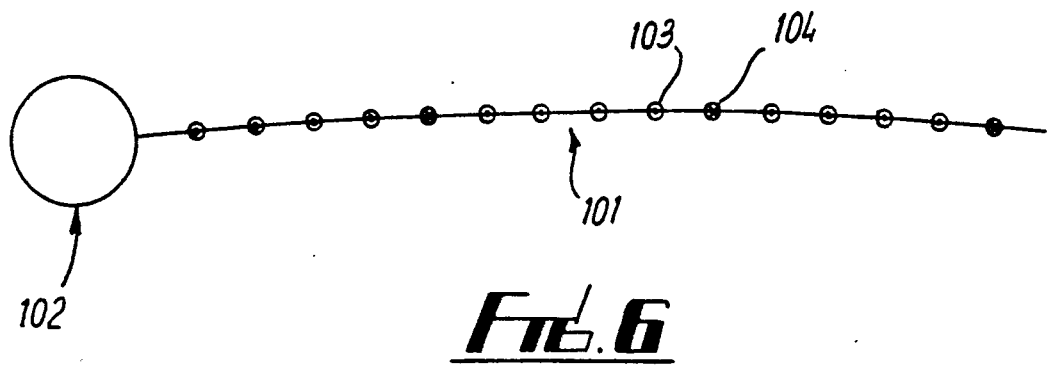
FIG. 6 illustrates an optical device having spaced sequential markings.

FIG. 6 illustrates an optical fibre 101 comprising an emitter/detector 102 at one end of the fibre 101 and a plurality of equally spaced markings 103, in the form of spots of light cured material, along the fibre length. The markings 103 are spaced apart by approximately 1 cm and each fifth mark 104 is coloured differently to the remaining marks 103 so as to ease countings of the marks 103 and 104.

Figure 7:
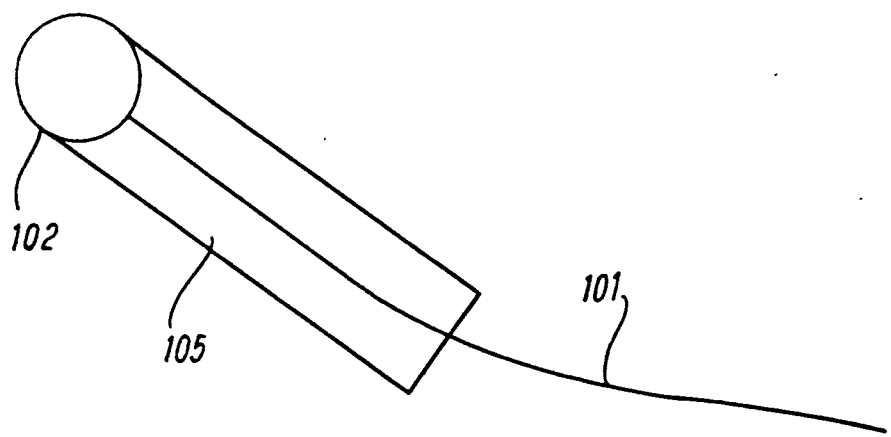
FIG. 7 shows a schematic diagram of a clad fibre.

FIG. 7 illustrates an embodiment of the optical device wherein a portion of fibre 101 adjacent the emitter/detector 102 is clad in a moulded material 105 to form a more robust and less easily damaged fibre. The moulded material is a light cured resin such as methyl methacrylate. The resin is not doped with scattering impurities.

Figure 8:
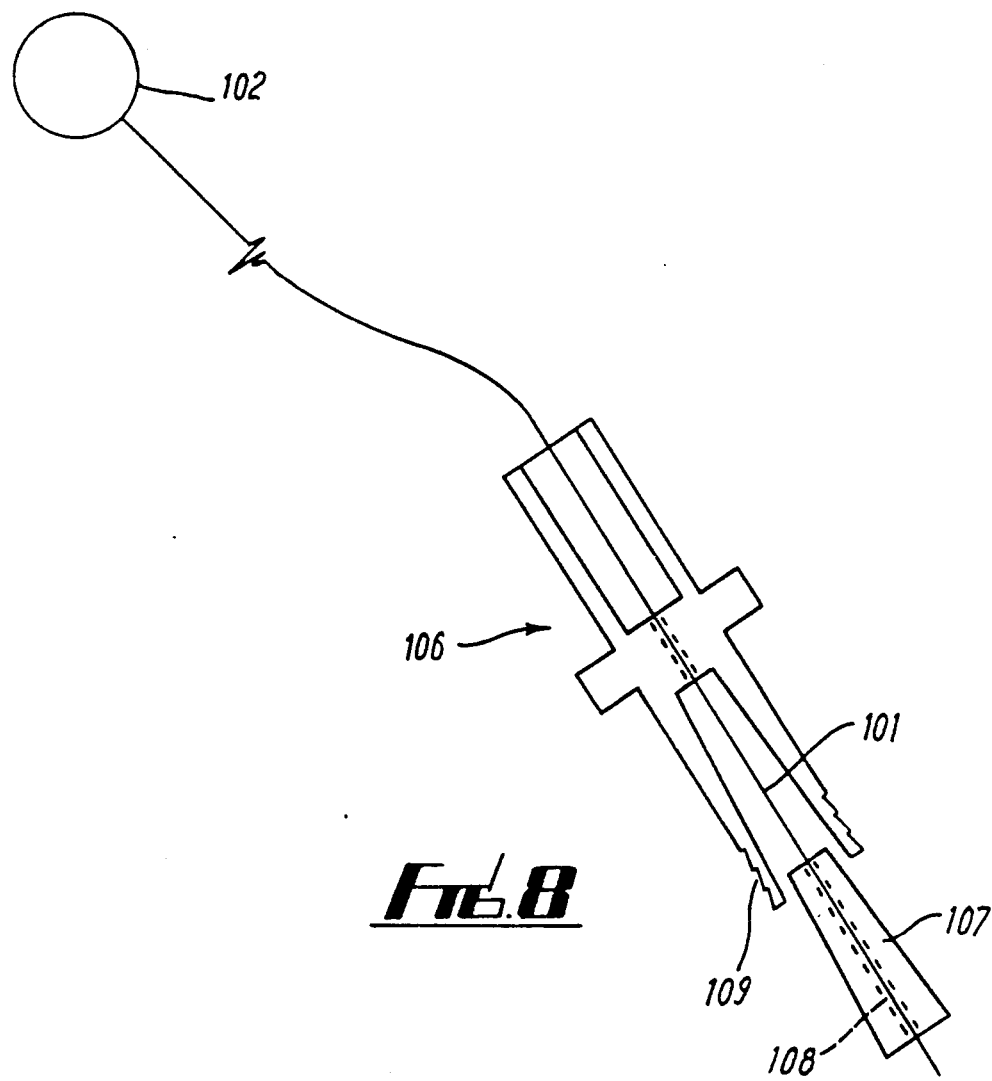
FIG. 8 shows a fibre mount in use with an optical device.

FIG. 8 shows a fibre mount comprising a standard syringe 106, the fibre 101 being passed through the centre of the syringe 106 and positioned centrally in the syringe 106 by a tapered plug 107 with a narrow central bore 108 which receives the fibre 101, when the plug 107 is in position. The output end of the syringe 106 has a screw-thread 109 to enable the syringe to be attached to an optical detector or standard optical mount, not shown.

This mount is of particular value when the optical device is inserted into the tissue by a method according to the second aspect of the present invention wherein a syringe needle is inserted into the tissue and the fibre 101 and emitter/detector 102 is passed through the syringe needle and into the tissue and needle is removed.

The syringe constitutes a low cost disposable optical mount for use with the optical device.

Figure 9B:
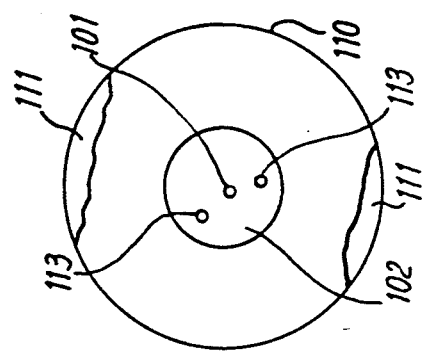
FIG. 9A shows a schematic diagram of a isotropic emitter and cylindrical detector in use in arterial plaque detection; and, FIG. 9B is a partial cross-sectional view along the line A—A in FIG. 9A.
Figure 9A:
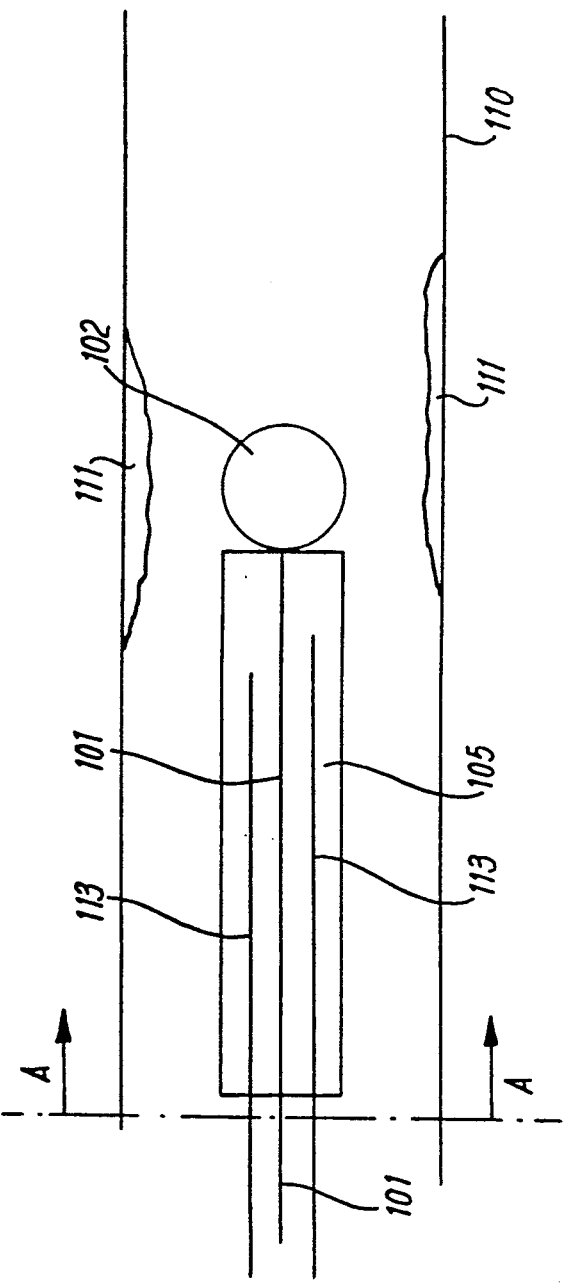

FIGS. 9A and 9B show an optical device being used in arterial plaque detection, the device comprising an optical fibre 101, one end of which includes an isotropic emitter 102, a cylindrical detector 105 in the form of a length of fibre 101 adjacent the emitter 102 clad in a light cured moulded material. The moulded material is transparent in the wavelength range covering both the florescence from arterial plaque and the initial input wavelength of an exetation laser.

The length of the cylindrical detector 105 enables the detection of light over a longer length of artery than would be possible with the isotropic detector.

The detector 105 is doped with scattering impurities to improve the percentage of the light which is transmitted along the fibre.

The isotropic emitter 102 emits light which is reflected by the artery wall 110 and arterial plaque 111 to a different degree. Thus detection of the quantity of reflected light will provide an indication of the quantity of arterial plaque. As arterial plaque 111 is fluorescent the isotropic emitter 102 may be used simply to excite fluorescence in the plaque 111 which may be detected by the cylindrical detector 105.

In order to provide a directional indication of plaque 111 position, a plurality of fibres 113 may be embedded in the cylindrical detector 105, the fibres 113 transmitting the detected light back to a monitor and thus providing a directional indication of plaque position 111 on the artery walls 110 due to the difference in quantity of light detected by the various fibres 113.

The cylindrical detector 105 is manufactured by placing the P.T.F.E. sheath over the fibre 111 adjacent the emitter 102 and inserting optically curable moulding material into the space between the sheath and the fibre 101. Light is then passed down the fibre to cure the material and the sheath is removed to disclose the detector 105.

In other embodiments of the invention fibres having different diameters may be used, for example 500 um.

Modifications and improvements may be incorporated without departing from the scope of the invention.

I claim:

1. A method of making an isotropic optical device, comprising providing an optical fibre having a free end; contacting said free end with a curable light-scattering material; passing optical radiation through the fibre to the free end; scattering said optical radiation among said light-scattering material by impingement of said optical radiation from the fibre on said light-scattering material; and curing said light-scattering material by said impingement of optical radiation thereon to form an isotropic light-scattering member.

2. A method according to claim 1, wherein the curable material is a chemical resin that has a catalyst that induces curing.

3. A method according to claim 1, wherein the material is cured by passing laser radiation along the optical fibre towards its free end.

4. A method according to claim 1, wherein the material is a dental fissure sealant.

5. A method according to claim 1, wherein the optical device includes two or more optical fibres, each of which has a free end which is contacted with the curable material.

6. A method of making an isotropic optical device, comprising providing an optical fibre having a free end; contacting said free end with a curable light-scattering material; passing optical radiation through the fibre to the free end; scattering said optical radiation amongst said light-scattering material by impingement of said optical radiation from the fibre on said light-scattering material; and curing said light-scattering material by said impingement of optical radiation thereon to form an isotropic light-scattering member; wherein before curing said light-scattering material in contact with the free end is in the form of a droplet suspended in a liquid.

7. A method according to claim 6, wherein the light-scattering material has a viscosity which enables it to be suspended in the liquid to produce a spherical probe end when the material has been cured.

8. A method according to claim 6, wherein the liquid is an organic liquid.

9. A method according to claim 8, wherein the organic liquid is paraffin.

* * * * *